United States Patent
Cohen

(10) Patent No.: US 7,754,489 B2
(45) Date of Patent: Jul. 13, 2010

(54) PROTOCOL FOR RISK STRATIFICATION OF ISCHEMIC EVENTS AND OPTIMIZED INDIVIDUALIZED TREATMENT

(75) Inventor: Eli Cohen, Skokie, IL (US)

(73) Assignee: Cora Healthcare, Inc., Niles, IL (US)

( * ) Notice: Subject to any disclaimer, the term of this patent is extended or adjusted under 35 U.S.C. 154(b) by 0 days.

(21) Appl. No.: 12/347,466

(22) Filed: Dec. 31, 2008

(65) Prior Publication Data

US 2009/0112483 A1 Apr. 30, 2009

Related U.S. Application Data

(63) Continuation of application No. 11/753,071, filed on May 24, 2007, and a continuation-in-part of application No. 11/608,174, filed on Dec. 7, 2006, which is a continuation-in-part of application No. 10/384,345, filed on Mar. 7, 2003, now Pat. No. 7,179,652, which is a continuation-in-part of application No. 09/591,371, filed on Jun. 9, 2000, now Pat. No. 6,613,573, which is a continuation-in-part of application No. 09/255,099, filed on Feb. 22, 1999, now Pat. No. 6,225,126.

(60) Provisional application No. 60/803,184, filed on May 25, 2006.

(51) Int. Cl.
*G01N 33/86* (2006.01)

(52) U.S. Cl. ............... 436/69; 436/63; 435/13; 600/369; 73/64.41

(58) Field of Classification Search .................. 436/63, 436/69; 422/73; 435/13; 600/368, 369; 73/64.41
See application file for complete search history.

(56) References Cited

U.S. PATENT DOCUMENTS

| | | | | |
|---|---|---|---|---|
| 6,225,126 B1 * | 5/2001 | Cohen et al. | ................... | 436/69 |
| 6,315,995 B1 * | 11/2001 | Pinsky et al. | ............. | 424/94.63 |
| 6,537,819 B2 * | 3/2003 | Cohen et al. | ................... | 436/69 |
| 6,613,573 B1 * | 9/2003 | Cohen | ......................... | 436/69 |
| 6,787,363 B2 * | 9/2004 | Cohen et al. | ................... | 436/69 |
| 6,797,519 B2 * | 9/2004 | Cohen et al. | ................... | 436/69 |
| 7,179,652 B2 * | 2/2007 | Cohen et al. | ................... | 436/69 |
| 7,192,726 B1 * | 3/2007 | Carr et al. | ...................... | 435/13 |
| 7,381,536 B2 * | 6/2008 | Gurbel | ......................... | 435/13 |

OTHER PUBLICATIONS

Platelet Reactivity in Patients and Recurrent Events Post-Stenting: Results of the Prepare Post-Stenting Study; Gurbel, et al.; J. Am Coll. Cardiol. 2005; 46; 1820-1826; Oct. 19, 2005.
Thromoelastography Maximum Amplitude Predicts Postoperative Thrmobotic Complications Including Myocardial Infarction; McCrath, et al.; Anesth Analg 2005; 100: 1576-83; 2005.

* cited by examiner

*Primary Examiner*—Maureen M Wallenhorst
(74) *Attorney, Agent, or Firm*—Anthony G. Sitko, PLC

(57) ABSTRACT

A hemostasis analyzer, such as the Thrombelastograph® (TEG®) hemostasis analyzer is utilized to measure continuously in real time, the hemostasis process from the initial fibrin formation, through platelet-fibrin interaction and lysis to generate blood hemostasis parameters. The measured blood hemostasis parameters permit preparation of an individualized assessment of ischemic event risk and individualized treatment of a subject.

5 Claims, 7 Drawing Sheets

BEFORE BIVALIRUDIN TREATMENT

AFTER BIVALIRUDIN TREATMENT

PROTOCOL FOR RISK STRATIFICATION OF ISCHEMIC EVENTS AND OPTIMIZED INDIVIDUALIZED TREATMENT

CROSS-REFERENCE TO RELATED APPLICATIONS

This application is a continuation of U.S. patent application Ser. No. 11/753,071 filed May 24 2007 entitled Protocol for Monitoring Direct Thrombin Inhibition, which is a continuation in part of U.S. patent application Ser. No. 11,608,174 filed Dec. 7, 2006 entitled Method of Evaluating Patient Haemostasis; which is a continuation-in-part of U.S. patent application Ser. No. 10/384,345 filed Mar. 7, 2003 entitled Protocol for Monitoring Platelet Inhibition, now U.S. Pat. No. 7,179,652; which is a continuation-in-part of U.S. patent application Ser. No. 09/591,371 filed Jun. 9, 2000 entitled Method and Apparatus for Monitoring Anti-Platelet Agents, now U.S. Pat. No. 6,613,573, which is a continuation-in-part of U.S. patent application Ser. No. 09/255,099, filed Feb. 22, 1999, entitled Method and Apparatus for Measuring Hemostasis, now U.S. Pat. No. 6,225,236, the disclosures of which are hereby expressly incorporated herein by reference.

TECHNICAL FIELD

This patent relates to protocols for monitoring patient hemostasis and in particular protocols for an individualized assessment of ischemic event risk and optimized individualized treatment of a subject.

BACKGROUND

Blood is the circulating tissue of an organism that carries oxygen and nutritive materials to the tissues and removes carbon dioxide and various metabolic products for excretion. Whole blood consists of a pale yellow or gray yellow fluid, plasma, in which are suspended red blood cells, white blood cells, and platelets.

An accurate measurement of hemostasis, i.e., the ability of a patient's blood to coagulate and dissolve, in a timely and effective fashion is crucial to certain surgical and medical procedures. Accelerated (rapid) and accurate detection of abnormal hemostasis is also of particular importance in respect of appropriate treatment to be given to patients being prepared for, undergoing or recovering from surgical procedures or suffering from hemostasis disorders and to whom it may be necessary to administer anticoagulants including direct or indirect thrombin inhibitors, antifibrinolytic agents, thrombolytic agents, anti-platelet agents, or blood components in a quantity which must clearly be determined after taking into account the circumstances of the surgery and/or the abnormal components, cells or "factors" of the patient's blood which may be contributing to the hemostasis disorder.

Hemostasis analyzer instruments have been known since Professor Helmut Hartert developed such a device in Germany in the 1940'S. One type of hemostasis analyzer is described in commonly assigned U.S. Pat. No. 5,223,227, the disclosure of which is hereby expressly incorporated herein by reference. This instrument, the TEG® hemostasis analyzer, monitors the elastic properties of blood as it is induced to clot under a low shear environment resembling sluggish venous blood flow. The patterns of changes in shear elasticity of the developing clot enable the determination of the kinetics of clot formation, as well as the strength and stability of the formed clot; in short, the mechanical properties of the developing clot. As described above, the initial fibrin formation, kinetics, strength and stability of the clot provides information about the ability of the clot to perform "mechanical work," i.e., resisting the deforming shear stress of the circulating blood; in essence, the clot is the elementary machine of hemostasis, and the TEG® analyzer measures the ability of the clot to perform mechanical work throughout its structural development. The TEG® system measures continuously all phases of patient hemostasis as a net product of whole blood components in a non-isolated, or static fashion from the time of test initiation until initial fibrin formation, through clot rate strengthening and ultimately clot strength through fibrin platelet bonding via platelet GPIIb/IIIa receptors and clot lysis.

Normal hemostasis process results in a three-dimensional network of polymerized fibrin fibers which together with platelet glycoprotein IIb/IIIa (GPIIb/IIIa) receptor bonding forms a final clot (FIG. 1a). A unique property of this network structure is that it behaves as a rigid elastic solid, capable of resisting deforming shear stress of the circulating blood. The strength of the final clot to resist deforming shear stress is determined by the structure and density of the fibrin fiber network and by the forces exerted by the participating platelets.

The clot that develops and adheres to the damaged vascular system as a result of activated hemostasis and resists the deforming shear stress of the circulating blood is, in essence a mechanical device, formed to provide a "temporary stopper," that resists the shear force of circulating blood during vascular recovery. The initial fibrin formation, kinetics, strength, and stability of the clot, that is its physical property to resist the deforming shear force of the circulating blood, determine its capacity to do the work of hemostasis, which is to stop hemorrhage without permitting inappropriate thrombosis. This is exactly what the Thrombelastograph® (TEG®) system was designed to measure, which is the time it takes for initial clot formation, the time it takes for the clot to reach its maximum strength, the actual maximum strength, and the clot's stability.

Thrombin is an enzyme that cleaves soluble fibrinogen into fibrin strands. It is also the most potent platelet activator and strongly and directly increases the expression and activation of platelet GPIIb/IIIa receptors. Platelets and fibrin cooperate to increase the mechanical strength of the clot in at least two ways. First, platelets provide node branching points to which fibrin strands attach, significantly enhancing clot structural rigidity. Secondly, the platelets exert a "tugging" force on the fibrin fibers, by the contractibility of platelet actomyosin, a muscle protein that is a part of a cytoskeleton-mediated contractibility apparatus. The force of this contractibility further enhances the strength of the fibrin/platelet structure and hence the resulting clot. Thus, thrombin's role in the hemostasis process, and in particular in mediating thromboembolic complications, is clear.

Despite a rather narrow therapeutic dosing range and a lack of a ready antidote, bivalirudin, a direct thrombin inhibitor, is being more widely used in percutaneous coronary interventional (PCI) procedures in place of heparin (an indirect thrombin inhibitor) since it has a more predictable anticoagulant effect. However, current methodologies such as the standard ACT tests based on kaolin do not accurately reflect anticoagulation by bivalirudin at higher doses raising the possibility of over-dosing patients. Ecarin based tests have been suggested as being better than ACT or other standard coagulation tests since ecarin directly activates prothrombin to a miezo-thrombin form, which has less feedback procoagulant activity than thrombin.

Along with thrombin, platelets play a critical role in mediating ischemic complications in prothrombotic (thrombophilic) patients. The use of GPIIb/IIIa inhibitor agents in thrombophilic patients or as an adjunct to PCI is rapidly becoming the standard of care. Inhibition of the GPIIb/IIIa receptor is an extremely potent form of anti-platelet therapy that can result in reduction of risk of death and myocardial infarction, but can also result in a dramatic risk of hemorrhage. The reason for the potential of bleeding or non-attainment of adequate therapeutic level of platelet inhibition is the weight-adjusted platelet blocker treatment algorithm that is used in spite of the fact that there is considerable person-to-person variability. This is an issue in part due to differences in platelet count and variability in the number of GPIIb/IIIa receptors per platelet and their ligand binding functions.

Since the clinical introduction of the murine/human chimeric antibody fragment c7E3 Fab (abciximab, ReoPro®), several synthetic forms of GPIIb/IIIa antagonists have also been approved such as Aggrastat® (tirofiban) and Integrilin® (eptifibatide), resulting in widespread and increasing use of GPIIb/IIIa inhibitor therapy in interventional cardiology procedures.

Before the introduction of the method and apparatus described in the afore-mentioned US Pat. No. 6,613,573, there was no rapid, reliable, quantitative, point-of-care test for monitoring therapeutic platelet blockade. Although the turbidimetric aggregometer test has been used to measure the degree of platelet GPIIb/IIIa receptor blockade in small clinical studies and dose-finding studies, its routine clinical use for dosing GPIIb/IIIa receptor antagonists in individual patients has not been feasible. Measurement by aggregometer is time-consuming (more than one hour), expensive to run, requires specialized personnel for its performance, and is not readily available around the clock; therefore it cannot be employed at the point-of-care for routine patient monitoring and dose individualization. To be clinically useful, an assay of platelet inhibition must provide rapid and reliable information regarding receptor blockade at the bedside, thereby permitting dose modification to achieve the desired anti-platelet effect.

The turbidimetric aggregometer test is based on the photometric principle, which monitors the change in the specimen's optical density. Initially, a minimal amount of light passes through the specimen, as functional platelets are activated by the turbidimetric test; platelet aggregation occurs via platelet GPIIb/IIIa receptor and fibrin(ogen) bonding as illustrated in FIG. 1a, and thus light transmission increases. When platelets are inhibited through GPIIb/IIIa receptor blockade, light transmission decreases proportionally.

Another commercially available system measures fibrinogen-platelet bonding using beads coated with a fixed amount of an outside source of "normal" fibrinogen. Therefore, this system uses a non-patient source of "normal" fibrinogen and cannot detect a patient in a prothrombotic state (hypercoagulable) due to a higher patient level of fibrinogen, or detect a hemorrhagic state (hypocoagulability) due to a low patient level of fibrinogen. Additionally, this system shows only bonding without detection of the breakdown of that bonding. Therefore, in the presence of thrombolysis, the assessment of platelet GPIIb/IIIa receptor blockade by the system may not be accurate.

Fibrinogen-platelet GPIIb/IIIa bonding (FIG. 1a) is the initial phase of platelet aggregation, or a primary hemostasis platelet plug, which is reversible; this goes on to form the final fibrin-platelet bonding (FIG. 1b). Thus it is not sufficient to measure only the initial stage of fibrinogen-platelet bonding, which may not accurately reflect final fibrin-platelet bonding via the GPIIb/IIIa receptor. While the turbidimetric and other photometric systems do detect initiation of platelet aggregation via fibrinogen-platelet GPIIb/IIIa receptor bonding (FIG. 1a), it may not accurately reflect final fibrin-platelet bonding via the GPIIb/IIIa receptor, which is non-reversible (FIG. 1b).

Significant among the limitations of systems that use beads coated with "normal" fibrinogen is that this "normal" fibrinogen may not reflect either the quantity or the functionality of a specific patient's own fibrinogen. Therefore, fibrinogen-platelet GPIIb/IIIa receptor blockade as measured by such systems is but a rough estimate of the patient's individual fibrinogen-platelet GPIIb/IIIa blockade of the initial phase of platelet aggregation.

This is a significant limitation in certain high risk patient subgroups, which may need treatment with a platelet inhibition agent, may have a higher or lower level of fibrinogen and thus would need an accurate assessment of platelet GPIIb/IIIa receptor blockade to reduce bleeding complications due to under assessment of platelet GPIIb/IIIa receptor blockade, or ischemic events due to over assessment of platelet GPIIb/IIIa receptor blockade. In addition, fibrinogen level and functionality may change during the trauma of interventional procedures. At this time it is imperative to make an accurate assessment of platelet GPIIb/IIIa receptor blockade in real time, during and following the procedure.

Thus, there is a need for a method and apparatus for evaluating contributors to patient hemostasis both in the presence and absence of therapies affecting hemostasis such as platelet inhibiting agents in the case of platelet hypercoagulability, thrombin inhibiting agents in the case of enzymatic hypercoagulability, and the like.

DETAILED DESCRIPTION

In accordance with the preferred embodiments of the invention, a hemostasis analyzer, such as the Thrombelastograph® (TEG®) hemostasis analyzer available from Haemoscope Corp., Niles, Ill., is utilized to measure continuously in real time, the hemostasis process from the initial fibrin formation, through platelet-fibrin GPIIb/IIIa bonding and lysis. While several specific hemostasis therapies are discussed herein in connection with the preferred embodiments of the invention, such as anti-platelet agent, direct or indirect thrombin inhibition, etc., it will be appreciated the invention has application in connection with virtually any hemostasis therapy. Moreover, it will be further appreciated that the invention has application for measuring the efficacy of coagulation enhancing agents.

In accordance with the preferred embodiments of the invention, utilization of the hemostasis analyzer in accordance with the inventive protocol permits: confirmation of the attainment of therapeutic level of a hemostasis therapy; individualized dosing assessments; illustration of the rate of enhancement or diminishment of the therapy with administration and evaluation of the interaction effect of a combination of therapies on patient hemostasis.

The present invention may use a hemostasis analyzer 10, such as the Thrombelastograph® (TEG®) hemostasis analyzer referenced above, to measure the clot's physical properties. An exemplary hemostasis analyzer 10 is described in detail in the aforementioned U.S. Pat. No. 6,225,126, and a complete discussion is not repeated here. Alterative devices for measuring hemostasis may be used such as those using contactless clot strength measurement as shown in U.S. patent application Ser. No. 11/383,567, or sample resonant excitation as shown in U.S. patent application Ser. No. 60/728,505, the disclosures of which are hereby expressly incorporated herein by reference. Any suitable whole blood analysis technique may be employed that analyzes the time to clot formation, rate of clot formation, clot strength and lysis.

Figure 2:
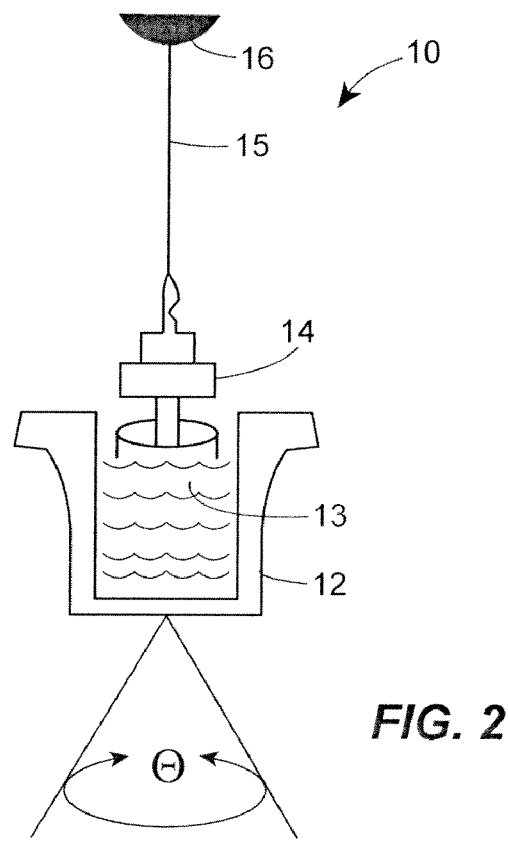
FIG. 2 is a schematic diagram of a hemostasis analyzer in accordance with a preferred embodiment of the invention.

With reference to FIG. 2, to assist in the understanding of the invention, however, a brief description of the hemostasis analyzer 10 is provided. The hemostasis analyzer uses a special stationary cylindrical cup 12 that holds a blood sample 13. The cup 12 is coupled to a drive mechanism that causes the cup to oscillate through an angle θ, preferably about 4°45". Each rotation cycle lasts 10 seconds. A pin 14 is suspended in the blood sample 13 by a torsion wire 15, and the pin 14 is monitored for motion. The torque of the rotating cup 12 is transmitted to the immersed pin 14 only after fibrin-platelet bonding has linked the cup 12 and pin 14 together. The strength of these fibrin-platelet bonds affects the magnitude of the pin motion, such that strong clots move the pin 14 directly in phase with the cup motion. Thus, the magnitude of the output is directly related to the strength of the formed clot. As the clot retracts or lyses, these bonds are broken and the transfer of cup motion is diminished.

The rotational movement of the pin 14 is converted by a transducer 16 to an electrical signal, which can be monitored by a computer (not shown in FIG. 2) including a processor and a control program.

The computer is operable on the electrical signal to create a hemostasis profile corresponding to the measured clotting process. Additionally, the computer may include a visual display or be coupled to a printer to provide a visual representation of the hemostasis profile. Such a configuration of the computer is well within the skills of one having ordinary skill in the art.

Figure 3:
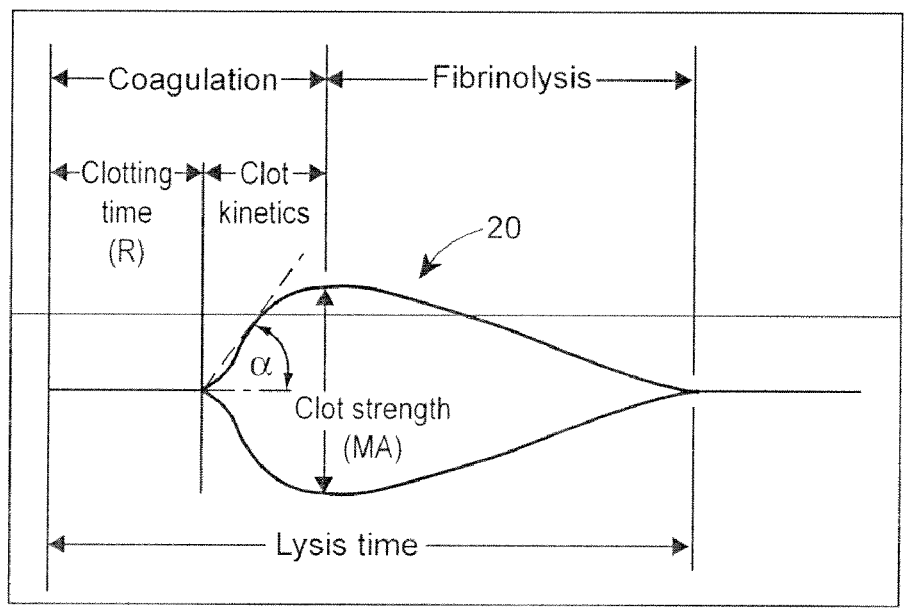
FIG. 3 is a plot illustrating a hemostasis profile generated by the hemostasis analyzer shown in FIG. 2.

As will also be described, based upon an assessment of the hemostasis profile, the computer, through its control program, may be adapted to provide dosing recommendations. As shown in FIG. 3, the resulting hemostasis profile 20 is a measure of the time it takes for the first fibrin strand to be formed, the kinetics of clot formation, the strength of the clot (measured in millimeters (mm) and converted to shear elasticity units of dyn/cm$^2$) and dissolution of clot. Table I, below, provides definitions for several of these measured parameters.

TABLE I

| | |
|---|---|
| R | R time is the period of time of latency from the time that the blood was placed in the TEG ® analyzer until the initial fibrin formation. |
| α | a measures the rapidity of fibrin build-up and cross-linking (clot strengthening) |
| MA | MA, or Maximum Amplitude in mm, is a direct function of the maximum dynamic properties of fibrin and platelet bonding via GPIIb/IIIa and represents the ultimate strength of the fibrin clot. |
| LY30 | LY30 measures the rate of amplitude reduction 30 minutes after MA and represents clot retraction, or lysis. |

Clinically, these measurements provide a vehicle for monitoring anticoagulation therapy (e.g. bivalirudin, heparin or warfarin, which elongate the R parameter and reduce α), thrombolytic therapy (e.g. tPA, streptokinase, urokinase, which increase LY30), effect of antifibrinolytics (e.g. ε-amino-caproic acid (Amicar®), trasylol (aprotinin), tranexamic acid (TX), which reduce LY30), effect of anti-platelet agents (e.g. abciximab (ReoPro®), eptifibatide (Integrilin®), tirofiban (Aggrastat®), which reduce MA), blood component transfusion therapy (which enhances the blood coagulation profile), thrombotic risk assessment in cancer and infection, high risk surgery and other conditions which could possibly lead to excessive clotting (hypercoagulable conditions) or excessive bleeding (hypocoagulable conditions). In accordance with the invention then, the hemostasis analyzer 10 is useful in testing the clinical efficacy of drug therapy to stop fibrinolysis, or the efficacy of thrombolytic drugs to monitor thrombolysis, efficacy of anti-platelet agents to monitor platelet inhibition, ischemic or bleeding complications.

Quantitatively, the hemostasis analyzer 10 and associated computer plot the strength of the clot against time, where the onset of clot formation, the reaction time (R), is noted (FIG. 3). This plot also indicates the maximum clot strength (or rigidity), MA, of a blood sample. MA is an overall estimate of platelet-fibrin GPIIb/IIIa bonding, which is used, for example, to guide post-operative blood platelet or fibrinogen replacement therapy.

The hemostasis parameters R, α, MA, and LY30 facilitate diagnosis of virtually any hemostasis disorder or evaluation of virtually any hemostasis therapy. For example, as between platelets and fibrin alone, an abnormally low MA implies that there is an abnormality in blood platelets (i.e., a quantitative or functional defect) and/or an abnormality in fibrinogen content in the blood. However, by keeping fibrinogen level and platelet number constant, any change in MA would reflect changes in platelet function. Therefore, by testing the same blood sample two ways, one with an anti-platelet agent and one without, the difference between the two MAs reflects the effect of the anti-platelet agent on platelet function. Similarly, isolating platelet contribution allows a determination of fibrinogen content, i.e., available functional fibrinogen.

Platelets play a critical role in mediating ischemic complications resulting in stroke and myocardial infarction. Inhibition of platelet function by anti-platelet agents (platelet-blocker drugs) such as aspirin, the antibody fragment c7E3 Fab, abciximab (ReoPro®), or clopidogrel, (Plavix®), can result in a dramatic reduction in the risk of death, myocardial infarction, or re-occlusion after percutaneous coronary intervention (PCI) or intra-arterial thrombolytic therapy (IATT). Administration of excessive amounts of anti-platelet agents could lead to life-threatening bleeding. Therefore, a precise estimate of platelet function inhibition in a given patient is very important for the monitoring of the drug therapy because of the narrow risk/therapeutic ratio with this class of drugs.

Using the above strategy, which keeps fibrinogen level and platelet number constant, it is possible to properly administer and monitor anti-platelet agents or modify their dosages, or to measure the contribution of fibrin to MA ($MA_{FIB}$) and by subtraction to measure the pure contribution of platelets to MA ($MA_P$) as $MA_P = MA - MA_{FIB}$.

Figure 11:
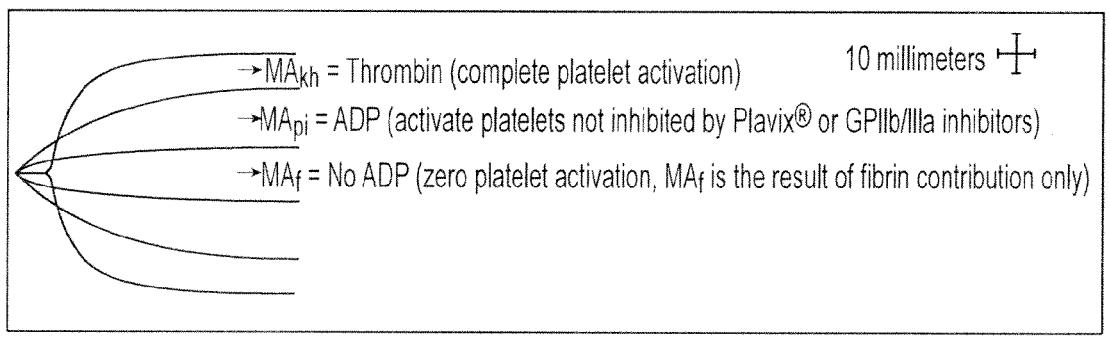
FIG. 11 illustrates several hemostasis profiles relating to the platelet activation described in connection with FIGS. 4-10.

Therefore, in accordance with one possible preferred embodiment of the invention, to properly monitor anti-platelet agents, the following procedure is followed:

1. The hemostasis analyzer 10, as it is commonly used, measures platelet function (MA or $MA_P$) that is stimulated by thrombin, a potent platelet activator that, as presently understood activates the GPIIb/IIIa receptor site through proteolytically activated receptors (PARs). To sensitize MA or $MA_P$ to a small inhibition of platelet function, platelet function is activated by a platelet agonist such as ADP that indirectly activates the GPIIb/IIIa receptor site (e.g., FIG. 11). Therefore, when running blood samples in the hemostasis analyzer 10 in this instance, formation of thrombin is inhibited with, for example, sodium citrate, heparin, hirudin, bivalirudin, etc., and ADP is used instead to activate the platelet function.
2. Unfortunately, thrombin is also involved in activating fibrinogen to fibrin conversion. Having inhibited thrombin formation in step 1, it is necessary to use another enzyme to activate fibrinogen. Batroxobin (such as available under the trade name Reptilase), whose sole function is to activate the fibrinogen to fibrin conversion, is a suitable enzyme. The clot is now stimulated by batroxobin (fibrinogen activation) and ADP (platelet activation). The strength of the clot is measured by MA, and the contribution of platelet function to the strength of the clot is measured by $MA_P$, as described above.
3. The clot that is formed by a fibrinogen activator like reptilase and a platelet activator like ADP is typically weaker than one developed by thrombin. Therefore, the torsion wire 15 described above may be selected to be sensitive to a weaker clot and to be able to measure the changes in MA and $MA_P$ due to the small effect of anti-platelet agents such as ReoPro®. Alternatively, activated Factor XIII (Factor XIIIa) may be added. Factor XIIIa is believed to cause bonding modification of crosslinked fibrin strands from hydrogen bonding to stronger covalent bonding, enhancing clot strength.

Based on the above, the following protocol may be implemented:

1. Torsion wire modification of the hemostasis analyzer 10 as necessary: by producing different strength torsion wires for various sensitivities to shear force to adequately measuring the effects of anti-platelet agents of various potencies may be measured. The sensitivity of the torsion wire is generally related to its gauge. For increased sensitivity, torsion wires having gauges to sense clot sensitivity in a range from about 150 to about 1000 dyn/cm2 are suitable for adaptation to the hemostasis analyzer described in the aforementioned U.S. Pat. No. 6,225,236.
2. Batroxobin-triggered agonist-activated blood sample: batroxobin (reptilase, Pentapharm) would be used (15 µl of reconstituted batroxobin reagent) and pre-added to the cup 12 to activate fibrinogen to fibrin. In addition to the batroxobin, ADP (2 µM final concentration) would be pre-added to the cup 12 along with 10 µl of Factor XIIIa. 340 µl of thrombin inhibited (e.g., citrated, heparinized, etc.) whole blood would be added to the pre-warmed cup 12 containing batroxobin, ADP and Factor XIIIa, and maximal clot strength would be measured providing an assessment of fibrin contribution and ADP activated platelet contribution to clot strength. In addition, clot strength of a control sample, with complete inhibition of the platelet contribution to clot strength ($MA_{FIB}$), would also be measured with batroxobin and Factor XIIIa but no platelet activator being added to the cup 12, providing an assessment of the contribution of fibrin in the absence of the augmenting effect of platelets to clot strength.

$MA_{PB}$ is measured before the patient is treated with the anti-platelet agent and $MA_{PA}$ is measured after treatment. Platelet inhibition due to the drug effect will be computed as follows:

$$MA_{PB} = MA_B - MA_{FIB}$$

$$MA_{PA} = MA_A - MA_{FIB}$$

Drug inhibition = $MA_{PB} - MA_{PA}$

For patients with high platelet activity (platelet hypercoagulability), who are at high risk of ischemic events, this method enables a means to administer and monitor anti-platelet agents or modify dosage to attain an individualized therapeutic level of platelet inhibition and minimize the patient's risk of ischemic events.

It will be appreciated by those having skill in the art that measuring clot strength as described above may require a torsion wire that is sensitive to the typically weaker clot formed under conditions of thrombin inhibition. However, different testing protocols may look to clots having strengths in ranges equal to or greater than typical thrombin supported clots. In such cases the torsion wire 15 will be selected to be sensitive to such stronger clots. Torsion wires of several gauges providing a range of sensitivities from about 100 dyn/cm$^2$ to 25,000 dyn/cm$^2$ therefore may be utilized.

It should be further appreciated that the invention has application to measuring other parameters of clot formation. For example, the hemostasis analyzer 10 measures the blood clotting process from the time of test initiation until the initial fibrin formation, through clot rate strengthening, and clot lysis. Therefore, in accordance in the invention, it is possible to measure the effect of the presence of heparin by evaluating the R parameter, which as described above indicates the inhibition in initial fibrin formation. It is also possible to measure the efficacy of drug therapy on thrombolytic activity by observing the parameter LY30, which indicates the rate of clot lysis.

Thrombin, which is the most potent platelet agonist, initiates the process of platelet aggregation. Thrombin is believed to act through a protease activated receptor (PAR) receptor-mediated response, which causes the expression of GPIIb/IIIa receptors. The following is a discussion of several factors and considerations related to this process.

It is well-documented that there is considerable person-to-person variability in the number of GPIIb/IIIa receptors per platelet and its ligand binding function. Furthermore, variable inhibition of GPIIb/IIIa function, in part due to the differences in platelet count, may occur after administration of a fixed, weight-adjusted dose of a platelet blocker. Higher risk patient subgroups, such as diabetic patients undergoing PCI, may require greater (loses of platelet inhibition than is currently being attained after weight-adjusted platelet blocker therapy, which at this time is not individualized to assure the attainment of adequate GPIIb/IIIa receptor blockade. The potential for hemorrhagic or ischemic events suggests the need for individualized assessment and projecting of needed dosing to assure the attainment of a therapeutic level of receptor blockade, in real time. The apparatus and method in accordance with the preferred embodiments of the invention provides this capability.

In contrast to direct platelet GPIIb/IIIa receptor inhibition agents, Plavix® (clopidogrel) is a platelet adenosine diphosphate (ADP) receptor antagonist, inhibiting a class of ADP receptors mediating activation of platelet GPIIb/IIIa receptors. Plavix® is taken orally, usually in the form of a loading dose of four 75 mg tablets followed by long-term therapy of one 75 mg tablet per day prior to and after PCI or for patients at high risk for ischemic events due to high platelet activity. The Plavix® algorithm dictates the same dosing regardless of patient weight or hemostatic profile. Consequently, treatment with Plavix® can result in increased bleeding or lack of attainment of an adequate therapeutic level of platelet inhibition. Therefore, there is a need to prescribe and monitor individualized dosing of both platelet GPIIb/IIIa and ADP receptor inhibition (PI) agents.

Thromboxane $A_2$ ($TxA_2$) activates the Thromboxane $A_2$ receptor. Once Thromboxane $A_2$ receptors are activated, they mediate the activation of GPIIb/IIIa receptors. Cyclo-oxygenase is the enzyme necessary in the production of Thromboxane $A_2$, and is inhibited by non-steroidal anti-inflammatory drugs (NSAID).

Figure 1A:
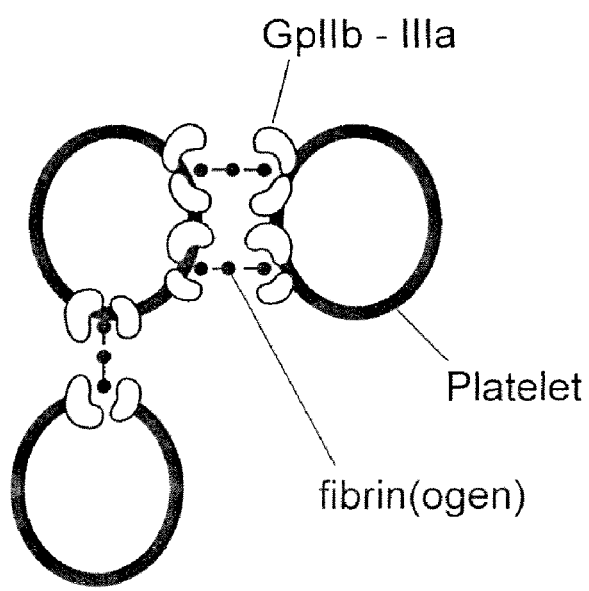
FIG. 1a is graphic illustration representing the initial phase of platelet aggregation.
Figure 1B:
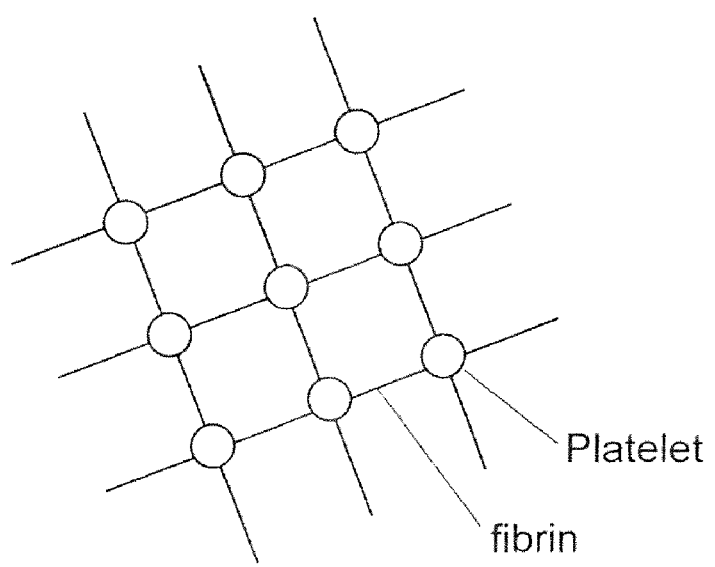
FIG. 1b is a graphic illustration representing fibrin-platelet bonding in final clot formation.

The result of the activated coagulation protein is the fibrin strand which, together with activated platelets at GPIIb/IIIa, forms fibrin-platelet bonding (FIG. 1b) to produce the final clot. Therefore for fibrin-platelet bonding to occur or to take place, platelet GPIIb/IIIa receptors have to be activated. Therefore platelet agonists are constricted toward activation of the GPIIb/IIIa receptor through PAR receptors, as by thrombin, or indirectly as by ADP and Thromboxane $A_2$. Consequently platelet inhibitor drugs are specifically targeted towards inhibiting these agonists as illustrate in FIGS. 4-10.

Figure 4:
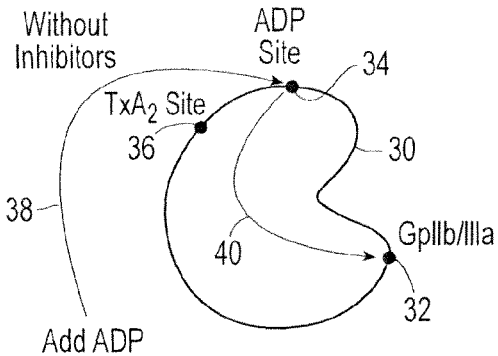
FIGS. 4-10 are schematic illustrations depicting platelet activation responsive to various agonist agents.
Figure 5:
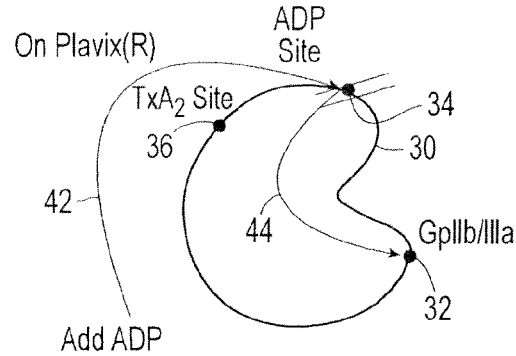
Figure 6:
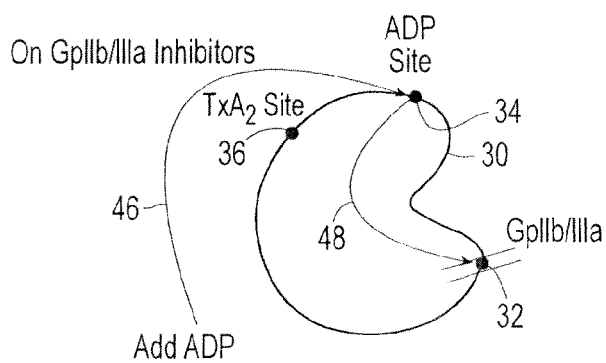
Figure 7:
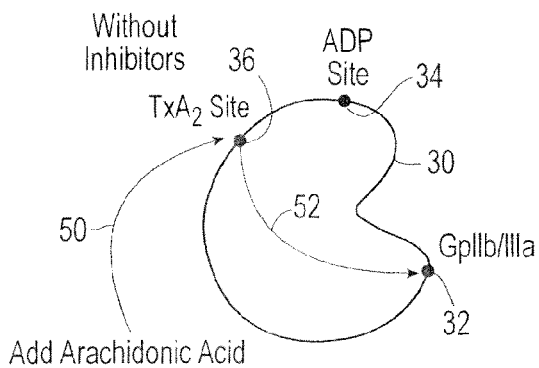
Figure 8:
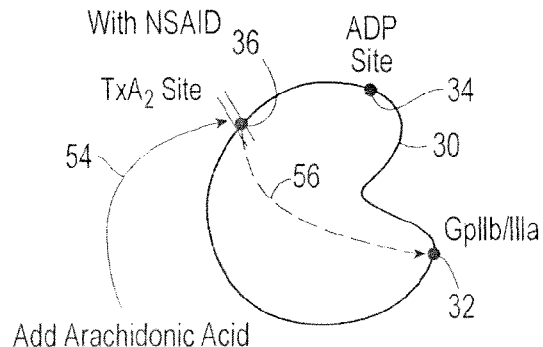
Figure 9:
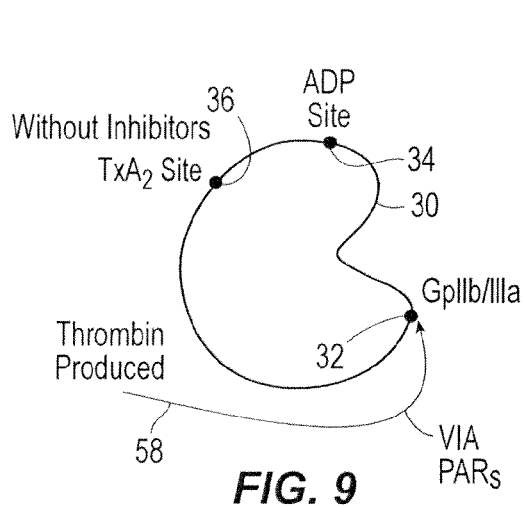
Figure 10:
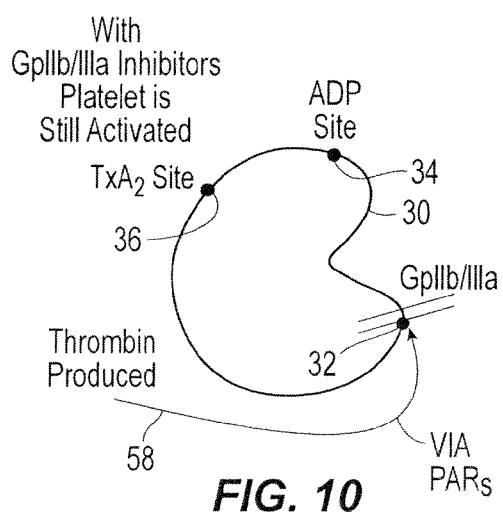

With reference to FIGS. 4-10, a platelet 30 has a GPIIb/IIIa receptor site 32, an ADP receptor site 34 and a $TxA_2$ receptor site 36. As shown in FIG. 4, addition of ADP agonist activates the ADP receptor site 34 (illustrated by arrow 38), which activates the GPIIb/IIIa receptor site (illustrated by arrow 40). A platelet adenosine diphosphate (ADP) receptor antagonist, such as Plavix®, inhibits the ADP receptor site 34 (arrow 42 in FIG. 5), and thus the GPIIb/IIIa site is not activated in response to the presence of the ADP agonist (phantom arrow 44). Therefore, in the presence of an ADP receptor antagonist, an ADP agonist only activates platelets that are not inhibited. The result is a reduction in clot strength, illustrated as the tracing $MA_{pi}$ in FIG. 11 as compared to the clot strength with complete platelet activation illustrated as the tracing $MA_{kh}$ in FIG. 11.

ReoPro®, Integrilin®, and Aggrastat® inhibit the GPIIb/IIIa receptor 32 directly. When the ADP agonist is added, it activates the ADP receptor 34 (arrow 46 in FIG. 6) but is stopped at the GPIIb/IIIa receptor (phantom arrow 48). Therefore, in the presence of GPIIb/IIIa inhibitors, only the non-inhibited platelets will be activated by the ADP agonist resulting in correspondingly reduced clot strength, e.g., $MA_{pi}$ illustrated in FIG. 11.

Thromboxane $A_2$ activates the platelet $TxA_2$ receptor 36 (arrow 50 in FIG. 7), which in turn activates the GPIIb/IIIa receptor 32 (arrow 52). Arachidonic acid (AA) is a precursor to Thromboxane $A_2$ and is converted to Thromboxane $A_2$ in the presence of Cyclo-oxygenase. Non-steroidal anti-inflammatory drugs (NSAID) inhibits Cyclo-oxygenase (arrow 54 in FIG. 8), and thus the GPIIb/IIIa site is also not activated in the presence of a $TxA_2$ agonist (phantom arrow 56) resulting in a corresponding reduction in clot strength, e.g., $MA_{pi}$ in FIG. 11. Therefore an AA platelet agonist can only activate the GPIIb/IIIa site 32 when NSAID is not taken.

Thrombin is the enzyme that cleaves soluble fibrinogen into fibrin strands. It is also the most potent platelet activator, strongly increasing the expression and activation of platelet GPIIb/IIIa receptors (arrow 58 in FIG. 9) through PARs receptors. It is believed that PAR-1 and PAR-4 at least provide this expression, but others may contribute. ReoPro®, Integrilin®, and Aggrastat® agents inhibit GPIIb/IIIa receptors responsive to ADP or $TxA_2$ agonists in vivo; however, they are not affective if administered in vitro as thrombin will still result in GPIIb/IIIa activation (arrow 58 in FIG. 10). Certain hemostasis assays, such as the above-referenced TEG® assay, may be arranged to produce thrombin in the process of clot formation. The increased expression and strong PARs receptor initiated activation of platelet GPIIb/IIIa by thrombin overcomes the GPIIb/IIIa inhibitors to provide a full platelet activation clot strength ($MA_{kh}$ in FIG. 11). In vivo, thrombin escaping into the circulation is immediately inhibited by endogenous anti-thrombin agents or by forming a complex molecule with endothelial thrombomodulin, localizing the hemostatic response to the site of injury. Ex vivo, for example when blood is placed in a testing apparatus, thrombin generation is continuous throughout the clot formation process. Due to the absence of endothelium, inhibitory activity is limited to the endogenous anti-thrombin agents in the sample and remains viable to cleave fibrinogen and mediate activation of GPIIb/IIIa receptors. Thus, as described herein, thrombin is suppressed to allow isolation and evaluation of other hemostasis factors and therapies.

Figure 12:
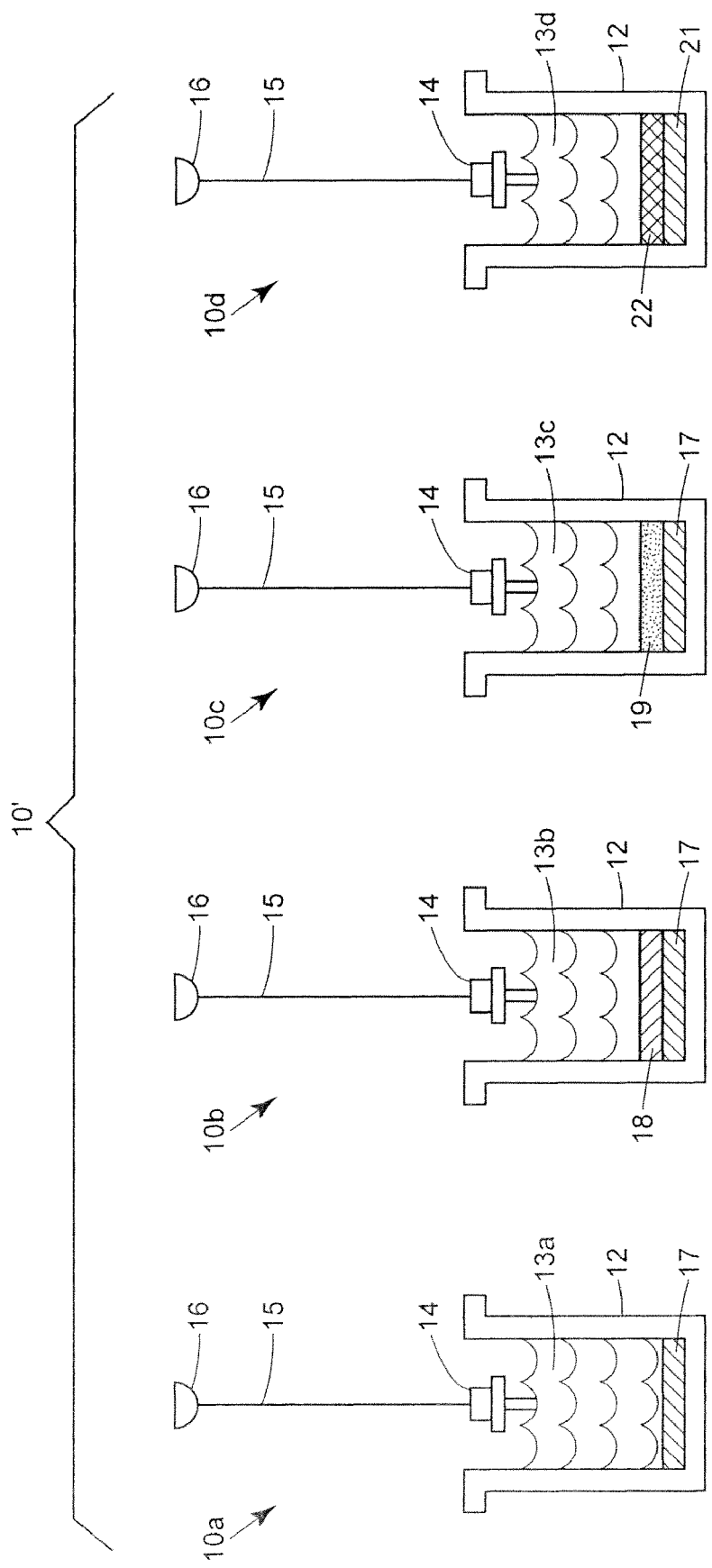
FIG. 12 is a schematic diagram of a hemostasis analyzer in accordance with an alternate embodiment of the invention.

With the foregoing discussion, it is therefore possible to further specify a protocol for monitoring platelet inhibitors, such as GPIIb/IIIa, ADP and Thromboxane $A_2$ platelet inhibitors. Referring to FIG. 12, an apparatus 10' may include a plurality of hemostasis analysis devices, such as the hemostasis analyzer 10 shown in FIG. 2, and four are shown as devices 10a, 10b, 10c and 10d, to respectively test corresponding blood samples 13a, 13b, 13c and 13d.

A first sample 13a of heparinized whole blood is prepared and loaded into the first hemostasis analyzer 10a. A fibrin activator 17, such as a combination of batroxobin and Factor XIIIa, is added to the sample cup 12. The activator 17 may be pre-added to the sample cup 12 or the cup 12 may be treated with the activator 17. Alternatively, the activator 17 maybe added to the blood sample 13a after it is added to the cup 12. About 10 μl of activator 17 is added to a 340 μl blood sample. The assay is completed and the resulting clot strength is measured. This clot strength may be referred to as $MA_f$, as it represents only the contribution of fibrin with substantially no platelet activation in view of the absence of any platelet agonist.

A second sample 13b of heparinized whole blood is prepared and is loaded into the second hemostasis analyzer 10b. It should be noted that a single cell hemostasis analyzer may be used serially for each of the assays, more than one single cell analyzer may be used, or multi-cell analyzers may be used. For example, the TEG® hemostasis analyzer in standard configuration has two testing cells, which may operate simultaneously. Two TEG® hemostasis analyzers may be used to perform each of the four assays according to this exemplary protocol or one TEG® hemostasis analyzer may be used. Moreover, the two TEG® hemostasis analyzers may be networked, making in essence a single four cell testing device.

For the second sample 13b, the activator 17 is added to the sample, and an ADP agonist 18 is also added in appropriate proportion to the second sample 13b. For example, 2 μM of ADP agonist may be added to a 340 µl second sample of heparinized whole blood. The assay is completed and the resulting clot strength is measured. This clot strength may be referred to as $MA_{pi1}$, as it represents the contributions of fibrin and platelets uninhibited by any administered ADP platelet inhibition agents.

A third sample 13c of heparinized whole blood is prepared and is loaded into a third hemostasis analyzer 10c. The fibrin activator 17 added to sample 13c, and a Thromboxane $A_2$ agonist 19 is added in appropriate proportion to the third sample 13c. For example, 10 µl of Arachidonic Acid (AA) may be added to a 340 µl third sample of heparinized whole blood. The assay is completed and the resulting clot strength is measured. This clot strength may be referred to as $MA_{pi2}$, as it represents the contributions of fibrin and platelets uninhibited by administered $TxA_2$ platelet inhibition agents.

A fourth sample 13d of heparinized whole blood is prepared and is loaded into a fourth hemostasis analyzer 10d. For the fourth sample 13d, heparinase 21 and kaolin 22 are used to neutralize the effect of the heparin in the fourth sample 13d and accelerate the thrombin expression, respectively. The assay is completed and the resulting clot strength is measured. This clot strength may be referred to as $MA_{kh}$, and it measures the maximum MA with platelet activation due to the use of heparinase and kaolin to neutralize the heparin in the sample 13d and to enable the production of thrombin which activates via the PARs receptors the GPIIb/IIIa receptors regardless of the inhibition of $TxA_2$, ADP, and GPIIb/IIIa receptors.

The value $MA_{pi}-MA_f$ measures the unique contributions of the uninhibited platelets by PI agents where platelet inhibition can be by the in vivo administration of agents, such as, Reopro®, Aggrastat®, Integrilin®, Plavix® and NSAIDs. A percentage reduction in MA due to platelet inhibition is then calculated for each of $MA_{pi1}$ and $MA_{pi2}$ according the equation:

Percent Platelet Activation=$[(MA_{pij}-MA_f)/MA_{kh}-MA_f)]*100$, where the value $MA_{kh}-MA_f$ measures the unique contributions of the fully activated platelets. Thus, the medical practitioner may observe the effect of platelet inhibition therapy, isolated into component effects, and make dosing recommendations accordingly. Alternatively, percent platelet inhibition may be determined as $100-[(MA_{pij}-MA_f)/MA_{kh}-MA_f)]*100$.

It will be appreciated that the sample cups 12 in the foregoing assays may be prepared in advance to contain the appropriate agents in accordance with the foregoing described protocol. In that regard, the sample cups may be color coded to identify the particular agents contained within the cup. Sets of sample cups 12 may be packaged to facilitate the assays. Still further, the agent materials, e.g., the activator 17, maybe distributed in color coded vials for ease of identification and for loading into the sample cups 12 either before or after the corresponding blood sample is loaded into the sample cup.

Assays in accordance with various preferred embodiments of the invention, such as the examples described above, may employ thrombin suppression, via in vitro or otherwise introduction of a suitable thrombin inhibitor, such as heparin. However, with thrombin suppression and a corresponding absence of thrombin contribution to hemostasis, e.g., cleavage of fibrinogen to form fibrin, additional reagents are required to compensate for the lack of thrombin and its contributing factors beyond platelet activation.

As noted, in accordance with preferred embodiments of the invention, it is possible to evaluate patient specific dosing and efficacy of virtually any hemostasis therapy by measuring and considering one or more of the hemostasis parameters. For example, it may be possible to monitor an anticoagulation therapy such as bivalirudin, heparin, warfarin or the like.

One exemplary protocol utilizes a sample, e.g., sample 13, that is obtained from a subject prior to administration of the anticoagulation therapy. Another sample is obtained at a first time period following administration of an anticoagulation therapy such as a direct thrombin inhibitor therapy like bivalirudin, heparin or warfarin. Each sample may be obtained into sodium citrate.

Figure 13:
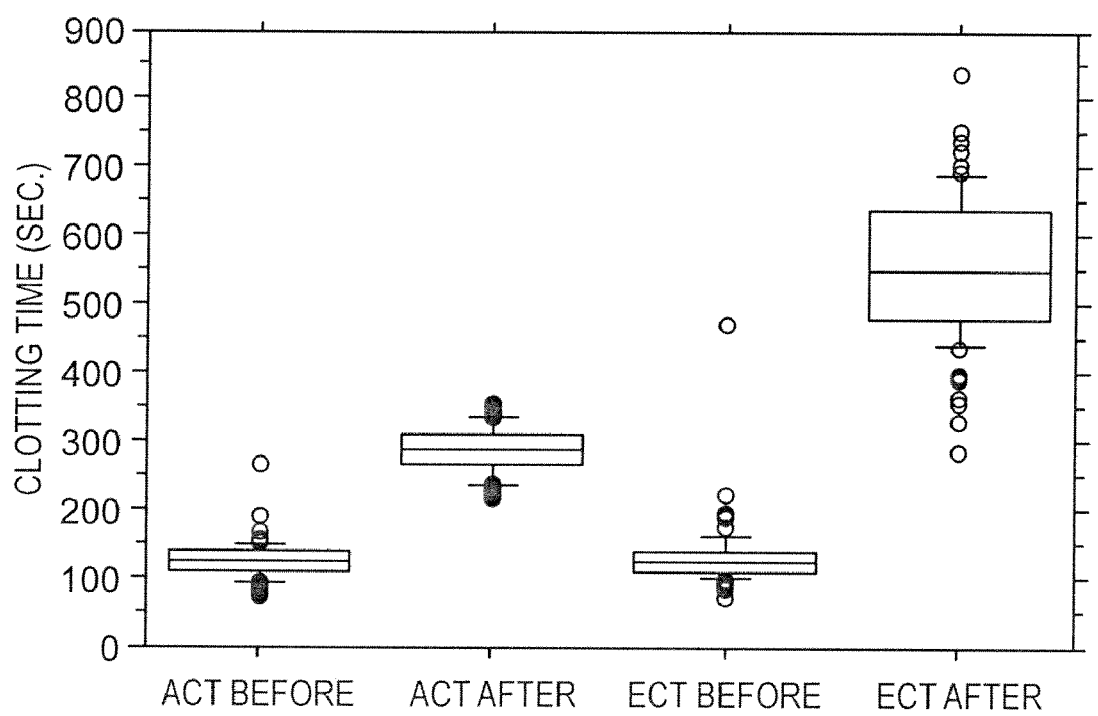
FIG. 13 is a chart illustrating initial clot formation times from a sampling of patients before and after administration of an anticoagulation therapy.
Figure 14A:
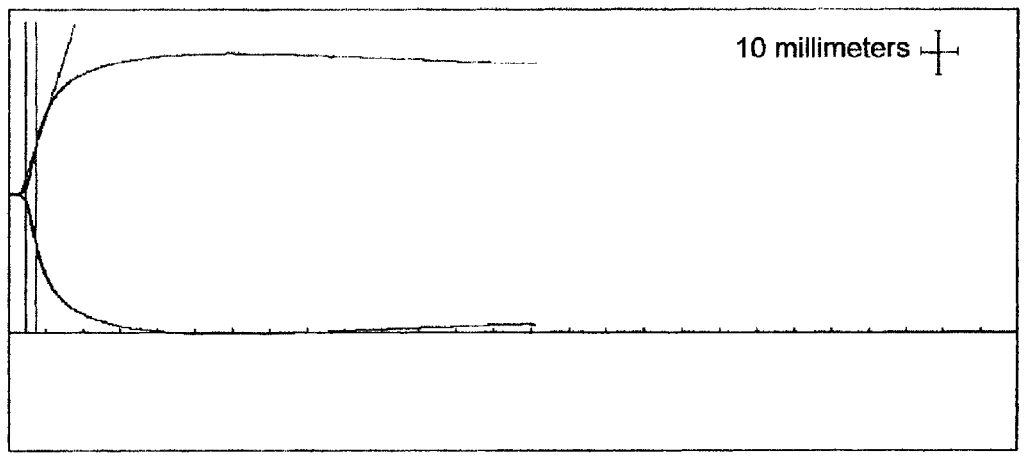
FIGS. 14a and 14b are hemostasis profiles of a subject before and after administration of an anticoagulation therapy.
Figure 14B:
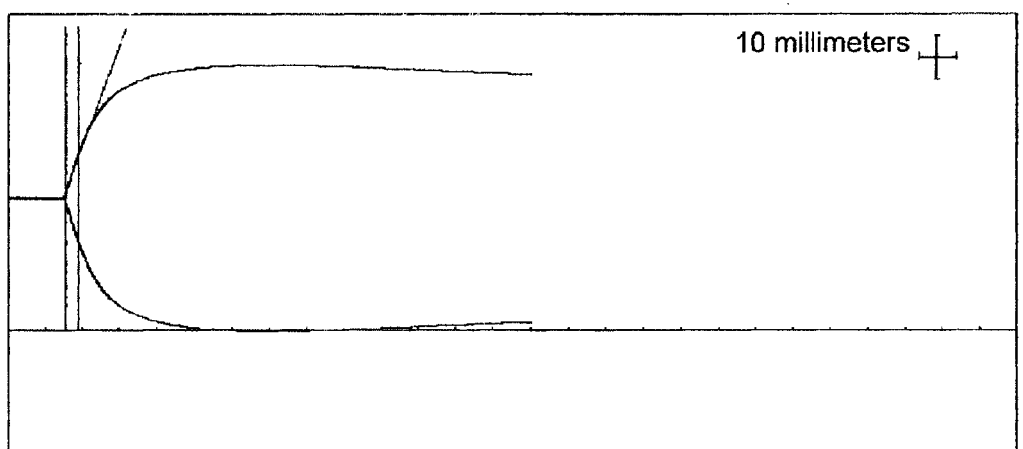

The sodium-citrated samples are recalcified, and an additional reagent is provided such as a prothrombin activator such as ecarin. The hemostasis analyzer 10 is used to measure the time to initial clot formation, R. FIG. 13 illustrates data for a sample of subjects showing time to initial clot formation R before in vivo administration of the anticoagulation therapy and after in vivo administration of the anticoagulation therapy FIGS. 14a and 14b illustrate tracings and, respectively, showing a typical set of hemostasis parameter data before in vivo administration of the anticoagulation therapy and after in vivo administration of the anticoagulation therapy. As the tracings and illustrate, apart from the change in the time to initial clot formation R, the tracings are otherwise typical, i.e., the rate of clot formation α, the clot strength MA and lysis, LY30 are otherwise within expected norms. Importantly, there exists correlation between the delay in initial clot formation and the dosing of the anticoagulation therapy. For the example illustrated in FIGS. 13, 14a and 14b, the delay in onset of clot formation shows a direct relationship to bivalirudin dosing. As described above, therefore, the whole blood hemostasis analyzer, such as the TEG® hemostasis analyzer, may be used to evaluate patient specific dosing of particular anticoagulation therapies for patients with enzymatic hypercoagulability.

For patients with accelerated initial clot formation (R, indicating enzymatic hypercoagulability as a result of rapid thrombin generation) who are at high risk of ischemic events, the method enables administration and monitoring of anticoagulation agents or modification of dosage to attain an individualized therapeutic level of anticoagulation and minimize the patient's risk of ischemic events.

Hemostasis is a very complex process, with multiple interactions among factors which include the procoagulant and anticoagulant proteins and cellular elements. Nothing in the hemostasis system is static or in isolation. Therefore, to reduce the probability of ischemic events, one has to look at the source of the prothrombotic state and determine whether it is due to enzymatic or platelet hypercoagulability or both. On an individual basis, one has to anticoagulate the patient, administer anti-platelet agents, or both in order to reach a balanced hemostasis where both ischemic events and bleeding are minimized The foregoing embodiments are described as generally applicable for post PCI patients, to screen for and prevent recurrence of ischemic events. However, the same procedure may be employed to screen initially for ischemic risk. Thus, the methodology may be employed in a prophylactic manner to assess initial risk of ischemic event and to inform a preventive therapy, such as the administration and dosage of anticoagulation agents.

The hemostasis analyzer 10 may include or be linked to a database. The database may contain correlation and/or normative data to which instant sample results may be compared by the processor to determine a patient specific dosing of the hemostasis therapy. The processor may be configured to make such a determination or, for example, when the database is remotely located from the hemostasis analyzer 10, a processor located with the database may be configured for such purpose.

It is presently understood that human platelets are activated by thrombin cleavage of PAR-1 and/or PAR-4 causing platelet aggregation (platelet-fibrin(ogen) bonding via GPIIb/IIIa receptors) and secretion. Antibody blockade of both PAR-1 and PAR-4 prevents virtually all thrombin-mediated platelet aggregation and secretion. This suggests that PAR-1 and PAR-4 mediate most, if not all, of the thrombin mediated signaling in human platelets. With PAR-1/PAR-4 inactivation and the thrombin's active site still intact, thrombin's procoagulant actions, e.g., cleavage of fibrinogen to form fibrin, activation of the serine protease FXI (Factor XI) and transglutaminase FXIII and other non-enzymatic coagulation factors remain intact. Thus, in the foregoing protocols, suppression of thrombin's platelet activating function by antibody blockade of PAR-1 and PAR-4 may be employed in the anti-platelet assay. At the same time, additional reagents are not required to preserve the pro-coagulant action of thrombin, e.g., cleave fibrinogen to fibrin by batroxobin and activate Factor XIII to Factor XIIIa for fibrin cross-linking and the like in the anti-platelet assay.

The invention has been described in terms of several preferred embodiments. One of skill in the art will appreciate that the invention may be otherwise embodied without departing from its fair scope, which is set forth in the subjoined claims.

I claim:

1. A method of preparing an individualized ischemic event risk assessment, the method comprising:

determining for a first blood sample portion obtained from a subject a first clot characteristic related quantitative indication of hemostasis of the first blood sample portion;

determining for the first blood sample portion obtained from the subject a first enzymatic related quantitative indication of hemostasis of the first blood sample portion; and determining a parameter indicative of the risk of the subject having an ischemic event based upon the first clot characteristic related quantitative indication and the first enzymatic related quantitative indication.

2. The method of claim 1, further comprising:

determining for a second blood sample portion obtained from the subject post in vivo administration of a hemostasis therapy a second clot characteristic related quantitative indication of hemostasis of the second blood sample portion;

optionally determining for the second blood sample portion obtained from the subject a second enzymatic related quantitative indication of hemostasis of the second blood sample portion; and determining a parameter indicative of the risk of the subject having an ischemic event based upon the second clot characteristic related quantitative indication and the second enzymatic related quantitative indication and determining the efficacy of the hemostasis therapy for the subject based upon the parameter.

3. The method of claim 2, wherein each of the first blood sample and the second blood sample are prepared including in vitro administration of an activator.

4. The method of claim 3, comprising comparing the first and the second clot characteristic related quantitative indications of hemostasis to correlation data and determining a dosing parameter of the hemostasis therapy in view of the correlation data.

5. The method of claim 1, wherein the quantitative indication comprises one of initial clot formation, clot strength, clot elasticity, rate of clot formation or rate of clot lysis.

* * * * *